(12) United States Patent
Ferrante et al.

(10) Patent No.: US 7,048,735 B2
(45) Date of Patent: May 23, 2006

(54) EXTERNAL FIXATION SYSTEM

(75) Inventors: Joseph Ferrante, Bartlett, TN (US); Anthony James, Bartlett, TN (US); David Castleman, Bartlett, TN (US); Ed Austin, Bartlett, TN (US); Kenneth Nelson, Memphis, TN (US)

(73) Assignee: Smith & Nephew, Memphis, TN (US)

( * ) Notice: Subject to any disclaimer, the term of this patent is extended or adjusted under 35 U.S.C. 154(b) by 262 days.

(21) Appl. No.: 10/067,052

(22) Filed: Feb. 4, 2002

(65) Prior Publication Data

US 2003/0149429 A1  Aug. 7, 2003

(51) Int. Cl.
*A61B 17/56* (2006.01)
*A61F 4/00* (2006.01)

(52) U.S. Cl. ............................................ 606/59
(58) Field of Classification Search .................. 606/53, 606/54, 59, 62, 55, 56, 58; 403/396, 90, 403/91; 248/68.1
See application file for complete search history.

(56) References Cited

U.S. PATENT DOCUMENTS

| | | |
|---|---|---|
| 554,284 A | 2/1896 | Lorang |
| 575,631 A | 1/1897 | Brooks |
| 1,271,792 A | 7/1918 | Standish |
| 1,563,242 A | 11/1925 | Tweit |
| 2,250,417 A | 7/1941 | Ettinger |
| 2,251,209 A | 7/1941 | Stader |
| 2,346,346 A | 4/1944 | Anderson |
| 2,391,537 A | 12/1945 | Anderson |
| 2,391,693 A | 12/1945 | Ettinger |
| 2,393,694 A | 1/1946 | Kirschner |
| 2,393,831 A | 1/1946 | Stader |
| 2,427,128 A | 9/1947 | Ettinger |
| 2,774,271 A | 12/1956 | Mano |
| 2,876,027 A | 3/1959 | Sulmonetti |
| 2,932,029 A | 4/1960 | Nicolo |
| 3,044,512 A | 7/1962 | Jones |
| 3,154,331 A | 10/1964 | Engelhardt |
| 3,195,380 A | 7/1965 | Bicks |
| 3,509,882 A | 5/1970 | Blake |
| 3,828,791 A | 8/1974 | Santos |
| 3,961,854 A | 6/1976 | Jaquet |
| 4,135,505 A | 1/1979 | Day |
| 4,170,990 A | 10/1979 | Baumgart et al. |
| 4,187,840 A | 2/1980 | Watanabe |
| 4,227,826 A * | 10/1980 | Conrad ...................... 403/371 |
| 4,364,381 A | 12/1982 | Sher et al. |
| 4,475,546 A * | 10/1984 | Patton ......................... 606/57 |
| 4,483,334 A | 11/1984 | Murray |
| RE31,809 E | 1/1985 | Danieletto et al. |
| 4,548,199 A | 10/1985 | Agee |

(Continued)

FOREIGN PATENT DOCUMENTS

CH          303453          5/1952

(Continued)

OTHER PUBLICATIONS

Smith & Nephew Brochure entitled "Only from Smith & Nephew The Original Ilizarov System," six pages (Jan. 1999).

(Continued)

*Primary Examiner*—Eduardo C. Robert
*Assistant Examiner*—Anuradha Ramana
(74) *Attorney, Agent, or Firm*—Kilpatrick Stockton LLP (57) ABSTRACT

An external fixation system having an improved fixation component for constructing a stable, adjustable fixation system that cooperates with other systems, and methods of use thereof.

67 Claims, 10 Drawing Sheets

U.S. PATENT DOCUMENTS

| | | | |
|---|---|---|---|
| 4,570,625 A | 2/1986 | Harris et al. | |
| 4,611,588 A | 9/1986 | Agee et al. | |
| 4,620,533 A | 11/1986 | Mears | |
| 4,635,634 A | 1/1987 | Santos | |
| 4,666,109 A | 5/1987 | Fallon et al. | |
| 4,696,293 A | 9/1987 | Ciullo | |
| 4,700,437 A | 10/1987 | Hoshino | |
| 4,730,608 A | 3/1988 | Schlein | |
| 4,785,694 A | 11/1988 | Burmester | |
| 4,848,368 A | 7/1989 | Kronner | |
| 4,922,856 A | 5/1990 | Sweeney, Jr. | |
| 4,998,935 A | 3/1991 | Pennig | |
| 5,062,844 A | 11/1991 | Jamison et al. | |
| 5,152,280 A | 10/1992 | Danieli | |
| 5,160,335 A | 11/1992 | Wagenknecht | |
| 5,167,725 A * | 12/1992 | Clark et al. | 428/680 |
| 5,207,676 A | 5/1993 | Canadell et al. | |
| 5,219,349 A | 6/1993 | Krag et al. | |
| 5,304,177 A * | 4/1994 | Pennig | 606/58 |
| 5,376,090 A | 12/1994 | Pennig | |
| 5,403,313 A | 4/1995 | Lin | |
| 5,405,347 A | 4/1995 | Lee et al. | |
| RE34,985 E | 6/1995 | Pennig | |
| 5,429,637 A | 7/1995 | Hardy | |
| 5,437,666 A | 8/1995 | Tepic et al. | |
| 5,443,465 A | 8/1995 | Pennig | |
| 5,451,225 A | 9/1995 | Ross, Jr. et al. | |
| 5,451,226 A | 9/1995 | Pfeil et al. | |
| 5,507,760 A * | 4/1996 | Wynne et al. | 606/159 |
| 5,545,162 A * | 8/1996 | Huebner | 606/57 |
| 5,586,983 A | 12/1996 | Sanders et al. | |
| 5,624,447 A | 4/1997 | Myers | |
| 5,658,283 A * | 8/1997 | Huebner | 606/57 |
| 5,662,648 A * | 9/1997 | Faccioli et al. | 606/54 |
| 5,662,649 A * | 9/1997 | Huebner | 606/57 |
| 5,662,650 A | 9/1997 | Bailey et al. | |
| 5,683,389 A | 11/1997 | Orsak | |
| 5,690,633 A | 11/1997 | Taylor et al. | |
| 5,702,389 A | 12/1997 | Taylor et al. | |
| 5,707,370 A * | 1/1998 | Berki et al. | 606/59 |
| 5,709,685 A | 1/1998 | Dombrowski et al. | |
| 5,728,095 A | 3/1998 | Taylor et al. | |
| 5,728,096 A | 3/1998 | Faccioli et al. | |
| 5,741,252 A | 4/1998 | Mazzio et al. | |
| 5,743,898 A | 4/1998 | Bailey et al. | |
| 5,746,741 A | 5/1998 | Kraus et al. | |
| 5,752,954 A | 5/1998 | Mata et al. | |
| 5,788,695 A * | 8/1998 | Richardson | 606/57 |
| 5,810,817 A * | 9/1998 | Roussouly et al. | 606/61 |
| 5,823,486 A | 10/1998 | Smith et al. | |
| 5,827,282 A | 10/1998 | Pennig | |
| 5,891,143 A | 4/1999 | Taylor et al. | |
| 5,891,144 A | 4/1999 | Mata et al. | |
| 5,931,837 A | 8/1999 | Marsh et al. | |
| 5,968,043 A | 10/1999 | Ross, Jr. et al. | |
| 5,971,984 A | 10/1999 | Taylor et al. | |
| 5,976,134 A * | 11/1999 | Huebner | 606/59 |
| 6,010,501 A | 1/2000 | Raskin et al. | |
| 6,024,745 A | 2/2000 | Paccioli et al. | |
| 6,030,386 A | 2/2000 | Taylor et al. | |
| 6,036,691 A * | 3/2000 | Richardson | 606/57 |
| 6,066,142 A | 5/2000 | Serbousek et al. | |
| 6,080,153 A | 6/2000 | Mata et al. | |
| 6,129,727 A | 10/2000 | Austin et al. | |
| 6,168,595 B1 | 1/2001 | Durham et al. | |
| 6,171,308 B1 | 1/2001 | Bailey et al. | |
| 6,203,575 B1 | 3/2001 | Farey | |
| 6,217,577 B1 | 4/2001 | Hofmann | |
| 6,221,072 B1 | 4/2001 | Termaten | |
| 6,238,400 B1 | 5/2001 | Bays | |
| 6,342,054 B1 | 1/2002 | Mata | |
| 6,386,786 B1 | 5/2002 | Perlman et al. | |
| 6,461,358 B1 | 10/2002 | Faccioli et al. | |
| 6,491,694 B1 | 12/2002 | Orsak | |
| 6,503,340 B1 * | 1/2003 | Gold et al. | 148/217 |
| 6,613,049 B1 | 9/2003 | Winquist et al. | |
| 6,616,664 B1 | 9/2003 | Walulik et al. | |
| 6,709,433 B1 | 3/2004 | Schoenefeld | |
| 2002/0026180 A1 | 2/2002 | Walulk et al. | |
| 2003/0149429 A1 | 8/2003 | Ferrante et al. | |

FOREIGN PATENT DOCUMENTS

| | | |
|---|---|---|
| CH | 02 709/94-3 | 9/1994 |
| DE | 375 151 | 5/1923 |
| DE | 1 935 977 | 2/1971 |
| DE | 1 603 999 | 5/1971 |
| DE | 27 45 504 A1 | 4/1979 |
| DE | 38 05 178 A1 | 8/1989 |
| DE | 38 23 746 A1 | 1/1990 |
| DE | 91 03 480.9 | 6/1991 |
| DE | 42 38 582 A1 | 5/1994 |
| DE | 295 12 917 U1 | 11/1995 |
| EP | 0 524 441 A1 | 6/1992 |
| EP | 0 524 441 A1 | 1/1993 |
| EP | 0 611 007 A1 | 8/1994 |
| EP | 0 700 664 A1 | 3/1996 |
| EP | 1 021 992 A2 | 7/2000 |
| FR | 2 665 353 A | 2/1992 |
| NO | 25934 | 6/1915 |
| SU | 167008 | 11/1965 |
| SU | 1491-492 A1 | 8/1988 |
| SU | 1572590 | 6/1990 |
| SU | 1572590 A1 | 6/1990 |
| WO | WO 88/01152 | 2/1988 |
| WO | WO 88/03395 | 5/1988 |
| WO | WO 94/18898 | 9/1994 |
| WO | WO 96/12443 | 5/1996 |
| WO | WO 97/10775 | 3/1997 |
| WO | WO 97/16128 | 5/1997 |
| WO | WO 97/16128 | 6/1997 |
| WO | WO 98/36698 | 8/1998 |
| WO | WO 99/22661 | 5/1999 |
| WO | WO 99/29247 | 6/1999 |
| WO | WO 00/40163 | 7/2000 |
| WO | WO 03/065911 | 8/2003 |

OTHER PUBLICATIONS

Hoffman II External Fixation System, 3 pages (Oct. 15, 2001) http://www.osteonics.com/howmedica/products/frames/prod2p.10.htm Search Report for European patent EP 92 11 0526.

International Search Report in related Application No. PCT/US03/39307.

"Epiphyseal Distraction Hemichondrodiatasis," by Roberto Aldegheri, et al., *Clinical Orthopaedics and Related Research*, No. 241, pp. 126-136, Apr. 1969.

"Use of an Articulated External Fixator for Fractures of the Tibial Plafond," *The Journal of Bone and Joint Surgery*, pp. 1498-1509, 1995.

Articulated External Fixation of Tibial Pilon Fractures: Effects on Ankle and Fragment Kinematics by D. C. Fitzpatrick, et al., 40th Annual Meeting, Orthopaedic Research Society, Feb. 21-24, 1994, New Orleans, Louisiana, one page.

ORTHOFIX Brochure entitled "Ankle Fusion Technique," one page, undated.

ORTHOFIX Brochure entitled "Arthrodiatasis Articulated Joint Distraction" by Dr. G. Trivella and Prof. M. Saleh, 8 pages (undated).

ORTHOFIX Operative Technique Brochure by Dr. J. L. Marsh and Dr. F. Lavini entitled "Distal Tibial and Pilon Fractures with the Radiolucent Ankle Clamp," pp. 1-21 (undated).

ORTHOFIX Operative Technique Brochure entitled "Distal Tibial and Pilon Fractures," by Dr. J. L. Marsh and Dr. F. Lavini, pp. 1-20, Oct. 16, 2002.

*Orthopedics Today*, vol. 14. No. 11, "Swedish cartilage repiart study offers hope, but more research is needed," pp. 1 and 43, Nov. 1994.

Hoffmann II External Fixation System, 3 pages (Oct. 15, 2001) http://www.osteonics.com/howmedica/products/frames/prod2p.10.htm.

Search Report for European patent EP 92 11 0526.

International Search Report in related Application No. PCT/US03/02712.

International Search Report in related Application No. PCT/US03/18067.

Patent Abstracts of Japan, vol. 017, No. 270 (C-1063), May 26, 1993 & JP 05 007604 A (Nagano Keikl Seisakusho), Jan. 19, 1993.

Agee, "External Fixation: Technical Advances Based Upon Multiplanar Ligamentotaxis," *Orthopedic Clinics of North America*, 24(2) (Apr. 1993).

"Epiphyseal Deistraction Hemichondrodiatasis, " by Roberto Aldegheri, et al., *Clinical Orthopaedics and Related Research*. No. 241, pp. 128-136, Apr. 1989.

"Use of an Articulated External Fixator for Fractures of the Tibial Plafond, " *The Journal of Bond and Joint Surgery*, pp. 1498-1509, 1995.

Articulated External Fixation of Tibial Pilon Fractures: Effects on Ankle and Fragment Kinematics by D.C. Fitzpatrick, et al., 40$^{th}$ Annuual Meeting, Orthopaedic Research Scoiety, Feb. 21-24, 1994. New Orleans, Louisiana, one page.

ORTHOFIX Brochure entitled "Ankle Fusion Technique," one page, updates.

ORTHOFIX Brochure entitled "Arthrodiatasis Articulated Joint Distraction" by Dr. G. Trivella and Prof. M. Saleh, 8 pages (undated).

ORTHOFIX Operative Technique Brochure entitled "Distal Tibial and Pilon Fractures with the Radiolucent Ankle Clamp," by Dr. J. L. March and Dr. F. Lavini, pp. 1-20, Oct. 16, 2002.

*Orthopedics Today* vol. 14, No. 11, "Swedish cartilage repair study offers hope, but more research is needed," pp. 1 and 43, Nov. 1994.

* cited by examiner

EXTERNAL FIXATION SYSTEM

FIELD OF THE INVENTION

This invention relates generally to methods, systems and devices for orthopedic external fixation and more particularly to an external fixation system having an improved fixation component for constructing a stable, adjustable fixation system that cooperates with other systems, and methods of use thereof.

BACKGROUND

Surgeons use external fixation systems regularly to treat certain bony skeletal injuries or conditions, such as acute fractures of the skeleton, soft tissue injuries, delayed union of the skeleton when bones are slow to heal, nonunion of the skeleton when bones have not healed, malunion of broken or fractured bones, congenital deformities resulting in malposition of bone, and bone lengthening, widening, or twisting. Treatment of these conditions often includes stabilization and reduction using an external fixation system. These systems may include a frame comprised of one or more of fixation components and one or more fixation elements. As used herein, fixation component refers to a device for positioning one or more parts of an external fixation system, and fixation element refers to one or more of a bar, rod, wire or pin used in an external fixation system. Wires may be threaded, beaded, or smooth, and pins may be threaded or smooth. Generally, one or more bone pins or wires are inserted into the tissue and bone and then the remainder of the fixation system is assembled. It is often important that a surgeon is able to place the external fixation system on the patient and then reduce the fracture in an expedited manner. Fracture patterns are infinite and may require the fixation system to move in multiple planes simultaneously in order to stabilize and reduce the fracture properly.

Current external fixation system designs vary, but generally include a mechanism for attaching at least one fixation element to a fixation component to form a construct, or frame, to support a fracture. In general, at least one pin or wire is drilled into the bone. Bone pins typically have one end that is either or both self-drilling and self-tapping, and have a diameter sufficient to resist bending. Bone wires are generally smaller in diameter. Bone pins or wires may be drilled completely through the bone, exiting the skin on the opposite side of the bone, called "transfixation pins," or may extend through the bony skeleton and out only one side of the limb, called "half pins." Current fixation components generally either connect a bar to a bar, a bar to a wire, or a bar to a pin. The frame of an external fixation system may include unilateral bars, which extend along the side of a patient's body, or circumferential or half rings, which encircle a patient's body member entirely or in part. Systems designed to use a circumferential ring or half ring include the ILIZAROV® brand system and the SPATIAL FRAME® brand system. The SPATIAL FRAME® brand system is described in U.S. Pat. No. 5,702,389, which is hereby incorporated by reference. Generally, circumferential and half rings have a rectangular cross-section.

When stabilizing and reducing a fracture using an external fixation system, it is important to properly align the bone fragments. Such alignment requires a fixation component that securely joins the pins and wires to the bars, but that is readily adjustable. In many cases, two pins are inserted below the fracture and two pins are inserted above the fracture. The surgeon then attaches a fixation component to each pin, bridging the fixation components together with rods, or bars. These bars form the frame of the external fixation system. As additional fixation components are added to the system in different planes, the frame become less adjustable. Current fixation systems permit a surgeon to choose the positioning of only two fixation components because after placement of two components, additional fixation components will only fit into set positions. During a procedure, it is often necessary to further reduce a fracture, which requires removal of the bars (and loss of positioning) and then replacement of the bars in the frame. Thus, additional reduction is difficult to achieve and requires reestablishment of optional position. Current systems are also highly dependent on accurate pin or wire placement. For example, if the pins or wires are angled incorrectly, the frame cannot be properly constructed One current external fixation component design includes two clamps that rotate in one plane to allow limited manipulation of the external fixation component. One jaw of each clamp of this design includes a toothed chip mechanism that has a surface with teeth similar to a poker chip. The teeth mate and lock when compressed, and thereby resist rotation in one plane after the clamps are in place. This poker chip design requires that the two fixation elements retained by the component are parallel to each other in at least one plane that is parallel to the poker chip surface, so that the angular relationship between the two fixation elements is always zero in that plane. Therefore, this system requires a parallel plane between the pin or wire and bar (or between two bars) for each fixation component. This requirement limits the system, as the positioning of each clamp is inhibited. Similar to other current designs, this design becomes substandard when several fixation components are used because it becomes constrained. In addition, the clamps of many current designs are adjacent a central shaft and are both locked upon tightening of a single screw, further constraining the system. Many current designs also allow for placement of the pins in the pin clamp of a fixation element only from the side and require a bent bar for placement of the system proximate the patient, if it is necessary to conform the system to the patient's anatomy. In addition, current designs use compression to hold the bar or pin in place, and may allow dislodgement of the pin or bar upon application of a great amount of pressure to the system when being placed.

Other prior art designs include circumferential rings or half rings, such as those in the ILIZAROV® and SPATIAL FRAME® brand systems. These specialized systems are often used for reduction of a fracture of the proximal tibia or distal femur. Generally, wires connected to half rings are used to stabilize a fracture. These specialized systems do not cooperate with general external fixation systems, and must be used separately.

Thus, there is a need for an external fixation system that provides a greater degree of freedom of rotation of the fixation components and therefore a more flexible frame construct, sequential locking of capture members, allowing greater adjustability, and cooperation with specialized fixation systems.

SUMMARY OF THE INVENTION

An external fixation system according to one embodiment of this invention allows manipulation of an external fixation component in any plane independent of the number of fixation components used, which is provided by the ability of the fixation component to rotate in multiple planes. Further, an improved fixation component according to one embodiment of this invention provides an external fixation system that does not bind or become constricted when numerous fixation components are used, providing the surgeon a stable system that is adjustable. One embodiment of a fixation component according to this invention includes two capture members, each adapted to receive a fixation element. The capture members are coupled such that one capture member is capable of rotation in three axes relative to the other capture member and wherein the coupling is adapted to secure the first and second capture members from rotation with a single activation.

One feature of one embodiment of this invention is a fixation component that provides a greater degree of freedom of rotation.

Another feature of one embodiment of this invention is a fixation component that simultaneously locks a capture member to a fixation element and locks the joint between two capture members.

Yet another feature is a fixation component that allows one capture member to be locked to retain a fixation element without forcing the second capture member also to be locked, allowing additional adjustment of position of the second capture member.

Another feature of one embodiment according to this invention is a fixation component having a locking mechanism that is not dislodged by application pressure.

Yet another feature of one embodiment of this invention is a fixation component that cooperates with specialized fixation systems.

DETAILED DESCRIPTION

Methods, systems and devices according to this invention seek to provide improved external fixation, including an improved fixation component allowing an increase in freedom of rotation, independent locking of capture members, a more stable, yet more flexible frame, and cooperation with specialized fixation systems. External fixation systems according to embodiments of this invention may include fixation components designed to retain one or more fixation elements. In general, the fixation components either connect a bar to a bar; a bar to a pin; a bar to a wire; or a bar to a circumferential or half ring. Each fixation component generally includes two capture members, and each capture member includes a base and a head.

One embodiment of a fixation component according to this invention includes a first capture member and a second capture member connected by a joint. Each capture member includes a channel, which allows attachment of a fixation element from the side. The first and second capture members are connected by a joint that allows each capture member to rotate with respect to the other capture member. The joint also allows rotation of up to 50° in any plane (25° each way), increasing the degree of freedom of rotation. In one embodiment, angulation is limited to 50° due to profile height constraints. However, in another embodiment more angulation may be provided. Thus, each capture member is provided three axes of rotation relative to the other capture member (e.g., typical "x," "y," and "z" axes). An external fixation system including fixation components according to this invention allows movement of either the bone, or components of the frame, along six separate axes—a combination of three orthogonal translational axes and three orthogonal rotational axes—so the system does not become constrained as additional components are added.

In one embodiment according to this invention, a fixation component having a unique joint allows simultaneous locking of one capture member and the joint. In addition, one capture member may be locked in place while the second capture member continues to freely rotate. In this manner, the surgeon is able to lock one capture member and continue to rotate the second capture member for final positioning. The surgeon is also able to loosen only one capture member to gain additional reduction, if required, without losing placement, as occurs with current systems when additional reduction is required.

Figure 7:
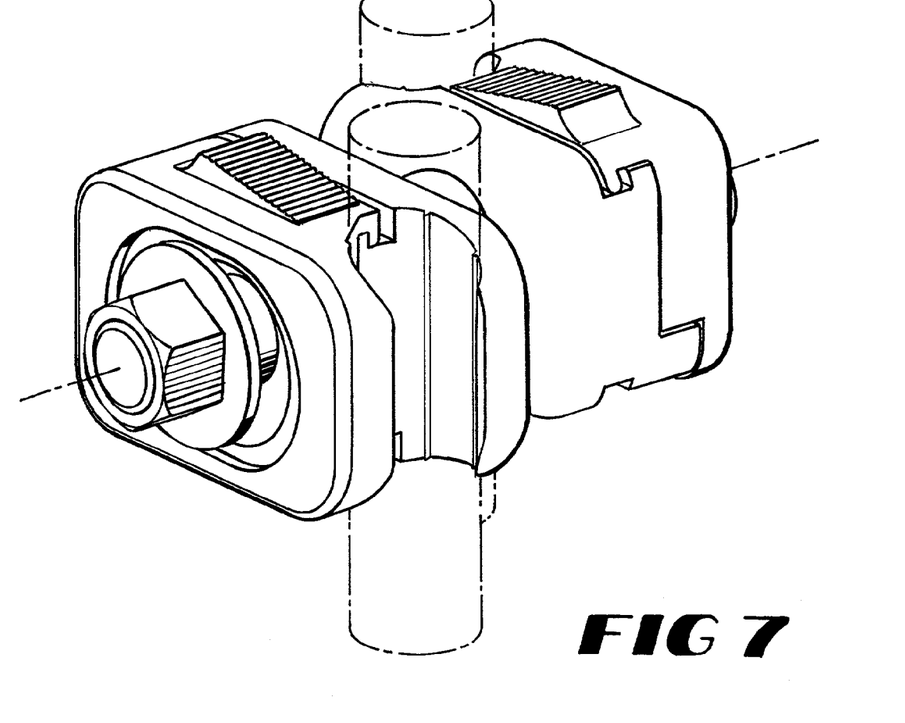
FIG. 7 is a perspective view of a fixation component according to an alternative embodiment of this invention.
Figure 8:
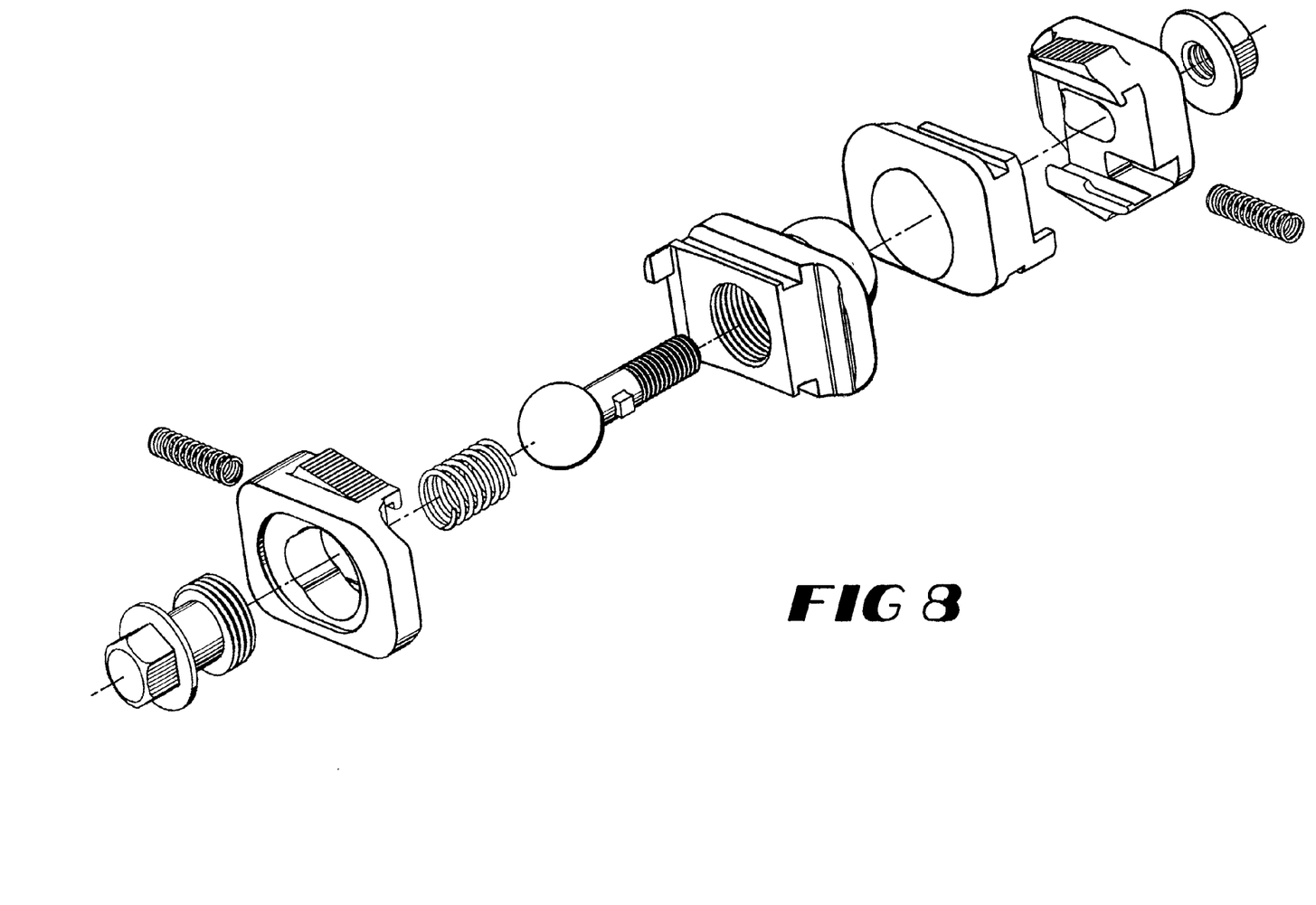
FIG. 8 is an exploded perspective view of the fixation component of FIG. 7.
Figure 9:
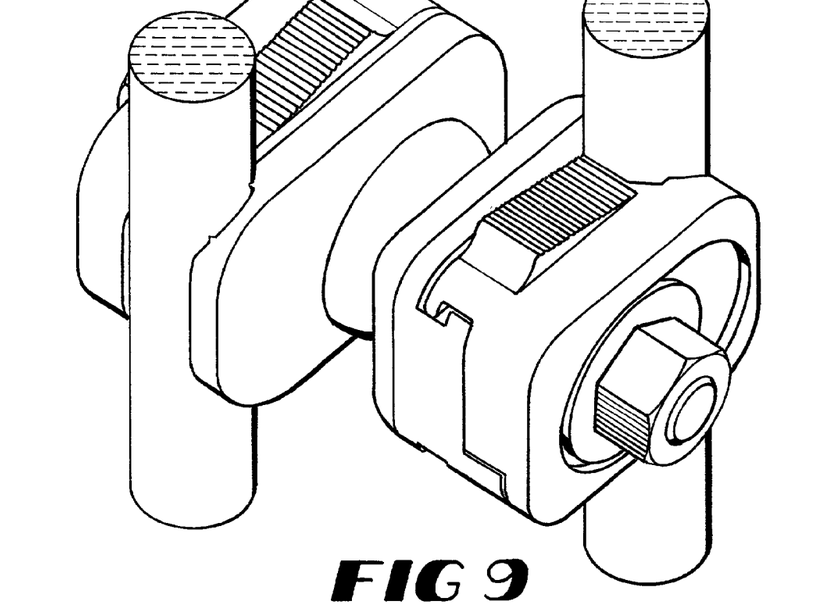
FIG. 9 is a perspective view of the fixation component of FIG. 7, with bars inserted in the capture members.

Consider one example of systems and devices according to this invention. As shown in FIGS. 1–6, a bar-to-pin fixation component 20 includes first capture member 24 and second capture member 22. First capture member 24 retains pin 26, while second capture member 22 is configured to retain bar 28, as shown in FIG. 3. The base 30 of first capture member 24 includes a groove 32, while the head 34 of first capture member 24 contains a wedge 36 (FIG. 4), which together are adapted to retain pin 26. Likewise, the base 38 and the head 40 of second capture member 22 include a groove 42 and a wedge 44, together adapted to retain bar 28. In one embodiment, groove 42 of second capture member 22 has splines 46, which provide rotational stability of bar 28 and penetrate the surface of bar 28 when second capture member 22 is tightened. Alternatively, the second capture member may be adapted to retain a pin and the first capture member may be adapted to retain a bar. In an alternative embodiment, both the first and second capture members are configured to retain a bar, as shown in FIGS. 7–9. In another embodiment, one capture member is adapted to retain a wire, while the other capture member is adapted to retain a bar. Additional embodiments are further described below.

Figure 1:
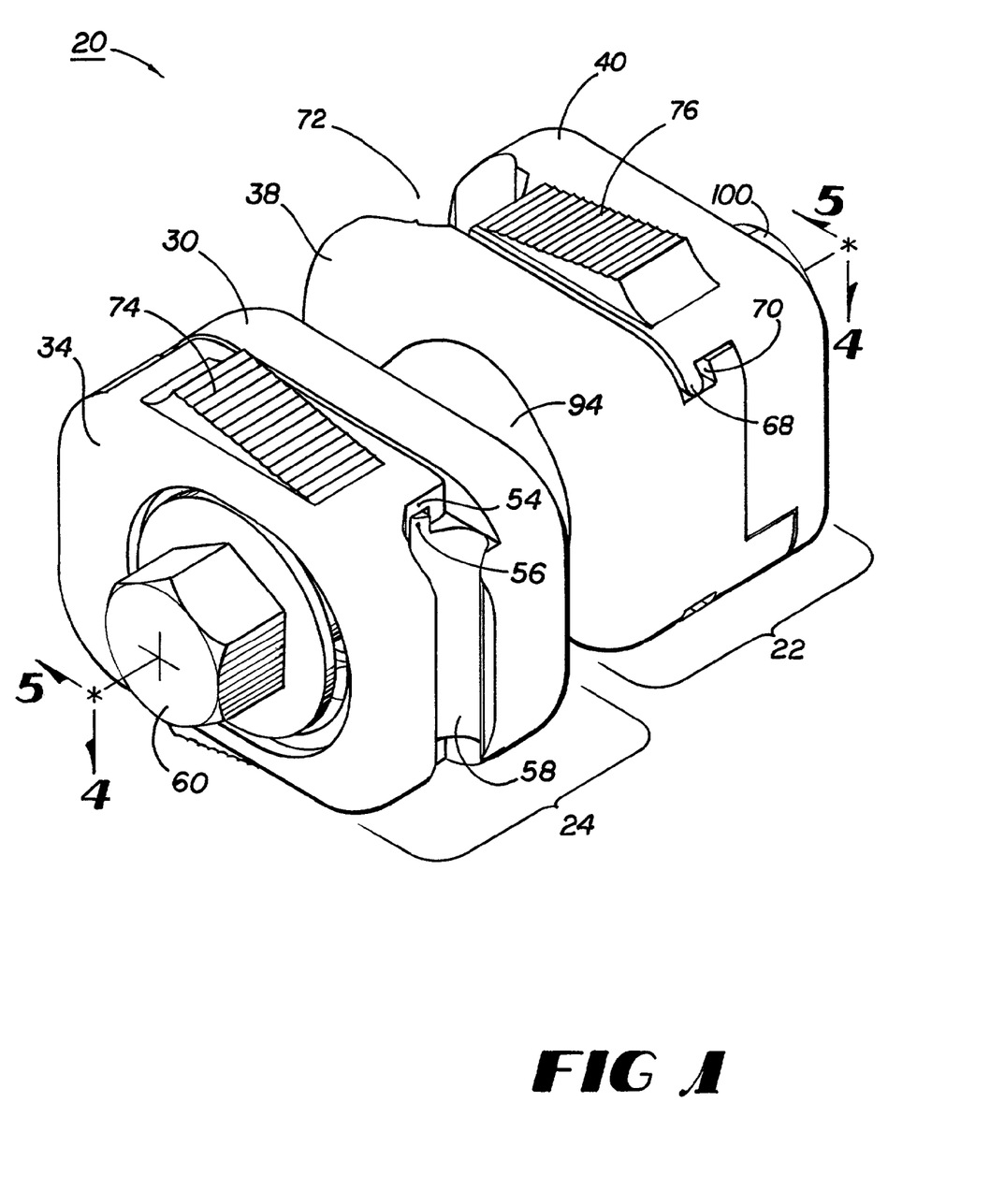
FIG. 1 is a perspective view of a fixation component according to one embodiment of this invention.
Figure 2:
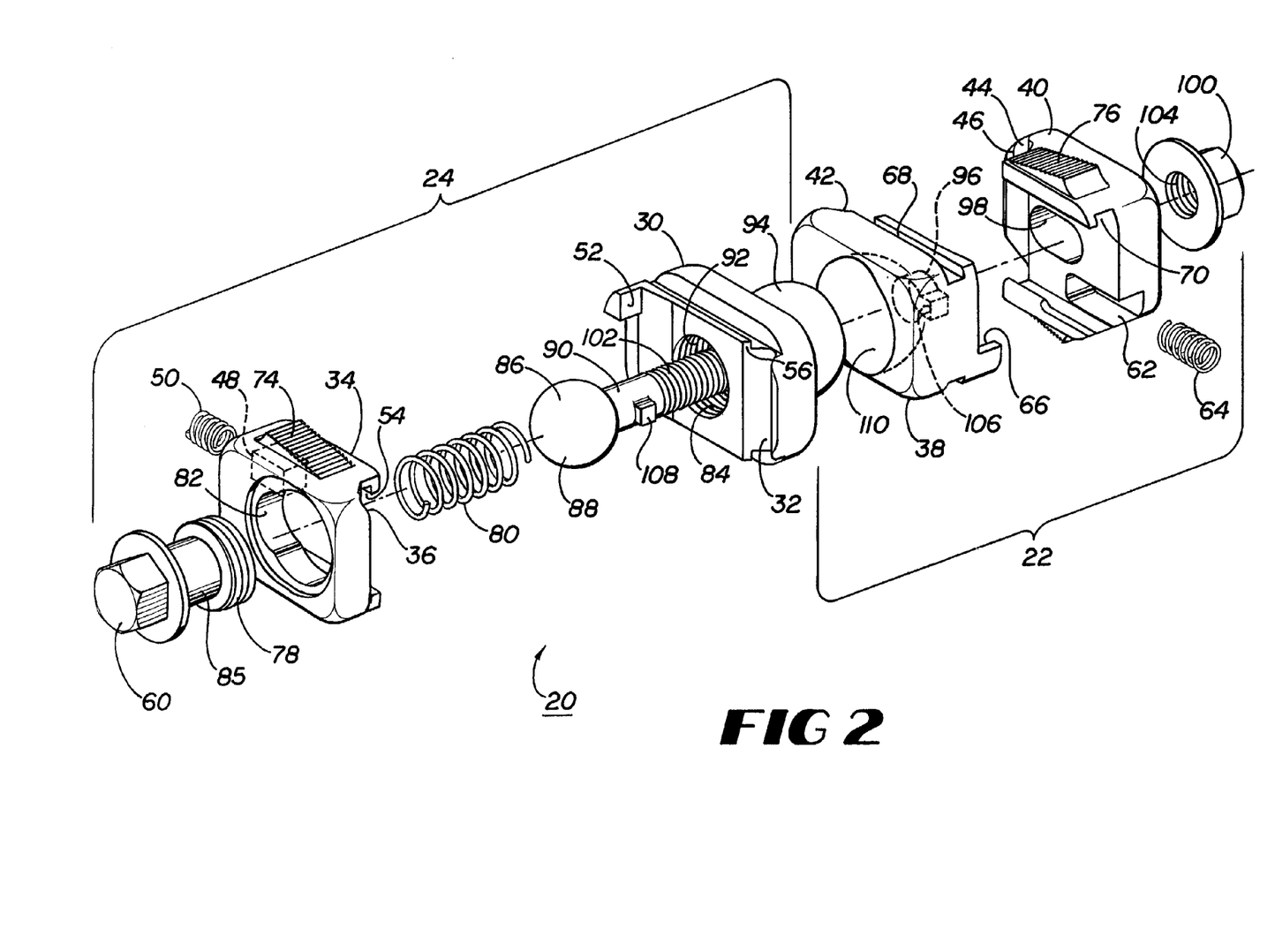
FIG. 2 is an exploded perspective view of the fixation component of FIG. 1.
Figure 3:
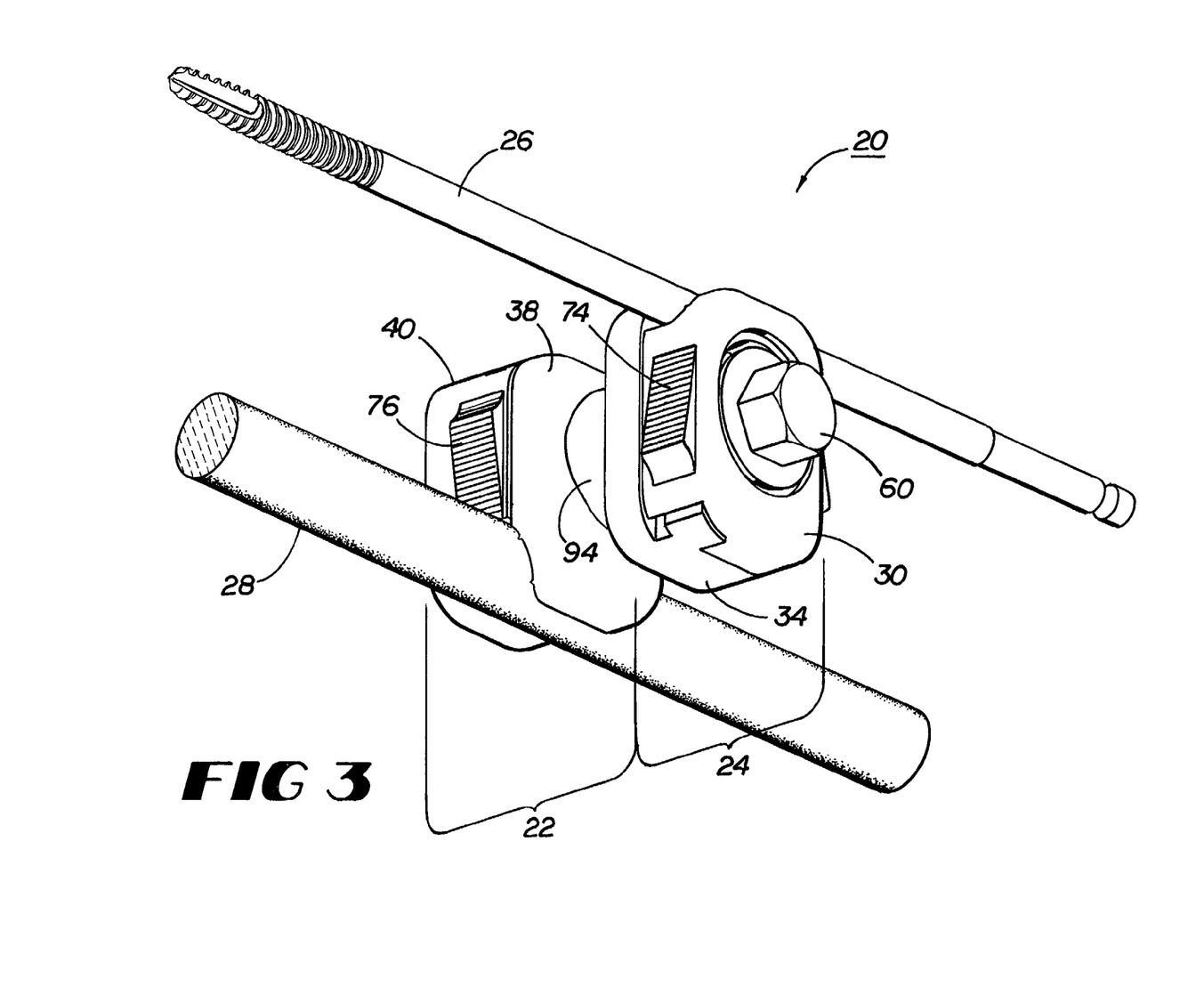
FIG. 3 is a perspective view of the fixation component of FIG. 1 with a pin and bar inserted.
Figure 4:
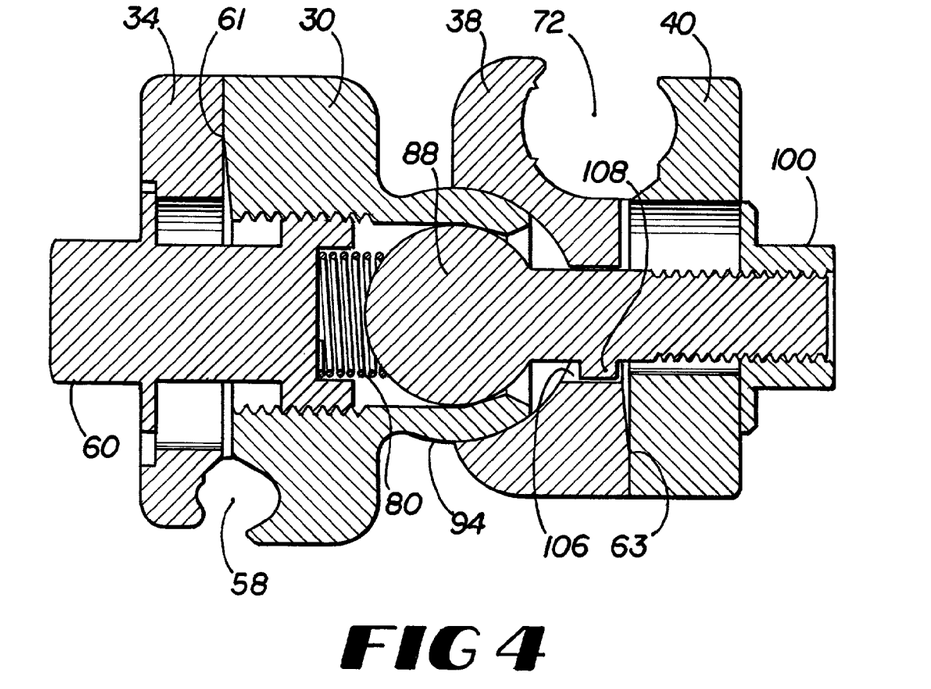
FIG. 4 is a cross-sectional view of the fixation component taken along lines 4—4 in FIG. 1.
Figure 5:
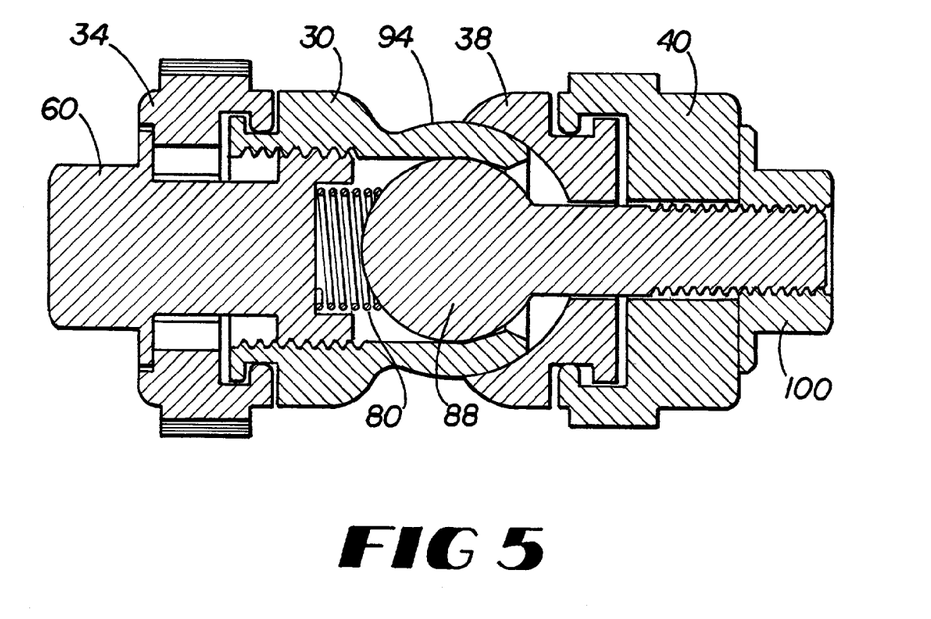
FIG. 5 is a cross-sectional view of the fixation component taken along lines 5—5 in FIG. 1.
Figure 6:
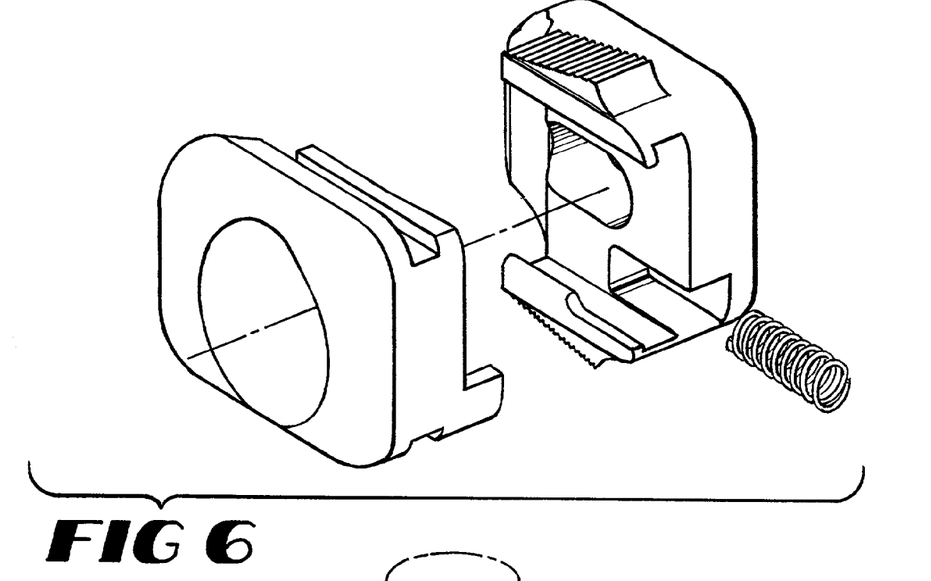
FIG. 6 is an exploded perspective view of the second capture member of FIG. 1.

As shown in FIG. 2, head 34 of first capture member 24 has a recess 48 adapted to receive spring 50, while base 30 of first capture member 24 includes stop 52. First track 54 on each side of head 34 slides in second track 56 on each side of base 30, allowing the head 34 and the base 30 of first capture member 24 to translate with respect to each other. In an alternative embodiment, second track 56 slides in first track 54. In one embodiment, one of first and second tracks 54, 56 is an L-shaped track, while the other track is shaped to receive the L-shaped track. As a force in a direction perpendicular to the pin is exerted against the groove 32 and wedge 36 of the first capture member 24, the head 34 moves, compressing the spring 50 against the extended portion of the base 30. The spring 50 compresses until it exerts a force in a direction perpendicular to the pin 26 that is equal and opposite to the force exerted against the wedge 36. At that point, the head 34 stops moving and holds the pin 26 in the groove 32 and wedge 36, which together form channel 58. After the pin 26 is located in the channel 58, the force of the spring 50 will temporarily hold the pin in position until the angular position of the channel 58 is set by tightening first fastener 60. Base 30 of first capture member 24 includes elevated portion 61, as shown in FIG. 4, forcing two points of contact between base 30 and head 34 in order to increase the holding power of first capture member 24. Base 38 of second capture member 22 also includes an elevated portion 63, also shown in FIG. 4, which increases the holding power of second capture member 22 in the same manner.

Second capture member 22 includes also includes a cartridge mechanism for retaining a bar 28. Head 40 of second capture member 22 has a recess 62 adapted to receive a spring 64, while base 38 of second capture member 22 includes stop 66. First track 68 on each side of head 40 slides in second track 70 on each side of base 38. In an alternative embodiment, second track 70 slides in first track 68. In one embodiment, one of first and second tracks 68, 70 is an L-shaped track, while the other track is shaped to receive the L-shaped track. Groove 42 and wedge 44 of second capture member form second capture member channel 72, which receives a bar 28. A bar 28 is retained in second capture member 22 in the same manner as first capture member 24 retains a pin 26.

In an alternative embodiment, one or both capture members may include two recesses for receiving two springs and two spring stops. In the embodiments shown, the recess, spring and stop are located on one side of the capture member. In an alternative embodiment, the recess, spring, and spring stop are in the middle of the capture member, or are on the other side of the capture member. In one embodiment, each head 40, 34 of the capture members 22, 24 includes grip surfaces 74, 76 for gripping and sliding heads 40, 34 in relation to bases 38, 30. In one embodiment, grip surfaces 74, 76 include ridges.

Threaded end 78 of first fastener 60 is adjacent a biasing element, such as center spring 80, and passes through keyhole aperture 82 in head 34 of first capture member 24, mating to internal threads 84 in base 30 of first capture member 24. Keyhole aperture 32 of head 34 if first capture member 24 allows reduced diameter neck 85 of first fastener 60 to translate within the aperture 82. Tightening of first fastener 60 locks the first capture member 24 and rigidly retains pin 26. In an alternative embodiment, the aperture 82 is circular, or any other suitable shape.

Connector 86 having end 88 and shaft 90 extends through keyhole aperture 92 in the base 30 of the first capture member 24. In one embodiment, the connector is a ball stud, as shown in FIG. 2, having a spherical end. The end 88 of connector 86 is received in planetary member 94 of base 30 of first capture member 24. As used herein, a planetary member refers to an object that is received in another object, and that receives another object within itself. In one embodiment, planetary member 94 is an outer sphere, as shown in the Figures. Shaft 90 of connector 86 extends through aperture 98 in base 38 of second capture member 22 and aperture 98 of head 40 of second capture member 22, and mates with second fastener 100. Threads 102 on shaft 90 of connector 86 mate with internal threads 104 of second fastener 100. Slot 106 in aperture 96 of base 38 of second capture member 100 is adapted to receive key 108 on the shaft 90 of the connector 86. Key 108 and slot 106 thus prevent rotation of the connector 86 within second capture member 22. In another embodiment, any suitable mechanism for preventing rotation of the connector is used. In other words, the connector fits through the base of the first capture member and the end is received in the planetary member of the base, while the shaft of the connector extends through both the base and head of the second capture member and threads to a second fastener. A planetary member, for example outer sphere 94, fits within cooperating surface 110, which is machined into the one side of the base 38 of the second capture member 22. Tightening of the second fastener 100 on the second capture member 22 draws the connector 86 into the planetary member 94, locking the second capture member and the joint to make it rigid. In one embodiment, one or both of the planetary member and cooperating surface may be tapered. For example, a taper of 10°, 15°, 20° or 30° may be used on each.

The joint mechanism described above allows the second capture member to rotate with respect to the planetary member of the first capture member, and allows the first capture member to grasp and lock a pin while permitting the second capture member to continue to rotate. Independent tightening of the capture members provides the surgeon flexibility to snap a fixation element to a capture member and then to manipulate the second capture member before locking the second capture member in order to achieve a more stable frame. In this manner, independent tightening of each capture member of the external fixation component allows more precise angular positioning.

Other embodiments, such as a bar-to-bar fixation component, shown in FIGS. 7–9, and a bar-to-wire fixation component, also may contribute to a more stable, more adjustable external fixation system. These embodiments function similarly to the bar-to-pin fixation component, with the capture members having a wedge and groove adapted to form a channel sized for receiving either a bar or a wire, depending on the component.

In one embodiment, a cartridge locking of the pin and bar is provided, as described above. However, in alternative embodiments, other one-piece designs may be used. For example, a solid piece of aluminum metal having the shape of the two part head and base cartridge construct of the two capture members may be used. This one-piece design includes a channel in each one piece capture member and a slot that extends close to the rear portion of the capture member. The slot causes the material to behave similar to a spring and allows the capture member to open when pressure is placed against it, so that a fixation element may be snapped into place in the channel.

Several mechanisms may be used to improve the locking capabilities of the joint. Coatings or elastic materials or alternate taper shapes may be applied to any of the articulating surfaces. For example, coatings or elastic materials or alternate taper shapes may be applied to one or both of the planetary member and cooperating surface so that a textured surface on either or both improves locking. In one embodiment, the cooperating surface is coated with SC729, a coating manufactured by Hitemco. In this embodiment, the cooperating surface is very rough and is made from tungsten cobalt carbide. In this embodiment, the value for slip increases to about 240 in.-lb., from about 140 in.-lb. without the coating. In an alternative embodiment, a mechanical locking pattern is applied. For example, splines and dimples may be added to one or both of planetary member and cooperating surface, providing teeth to grab when locking, thereby improving the locking function. A 30 degree chosen taper configuration on the inside of the planetary member mating surface uses a taper design to achieve torque strength of up to 200 in.-lb.

Figure 10:
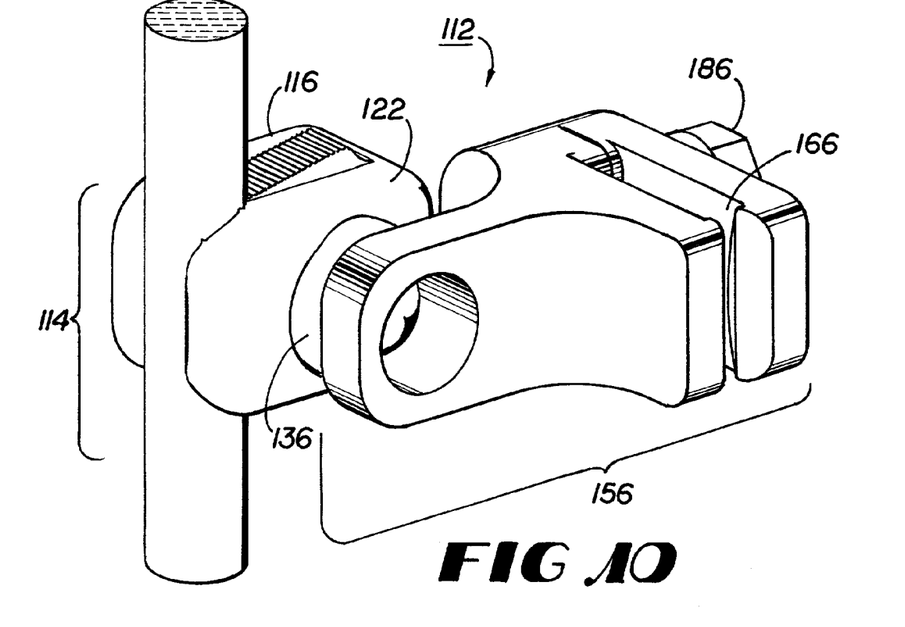
FIG. 10 is a perspective view of a fixation component according to an alternative embodiment of this invention.
Figure 11:
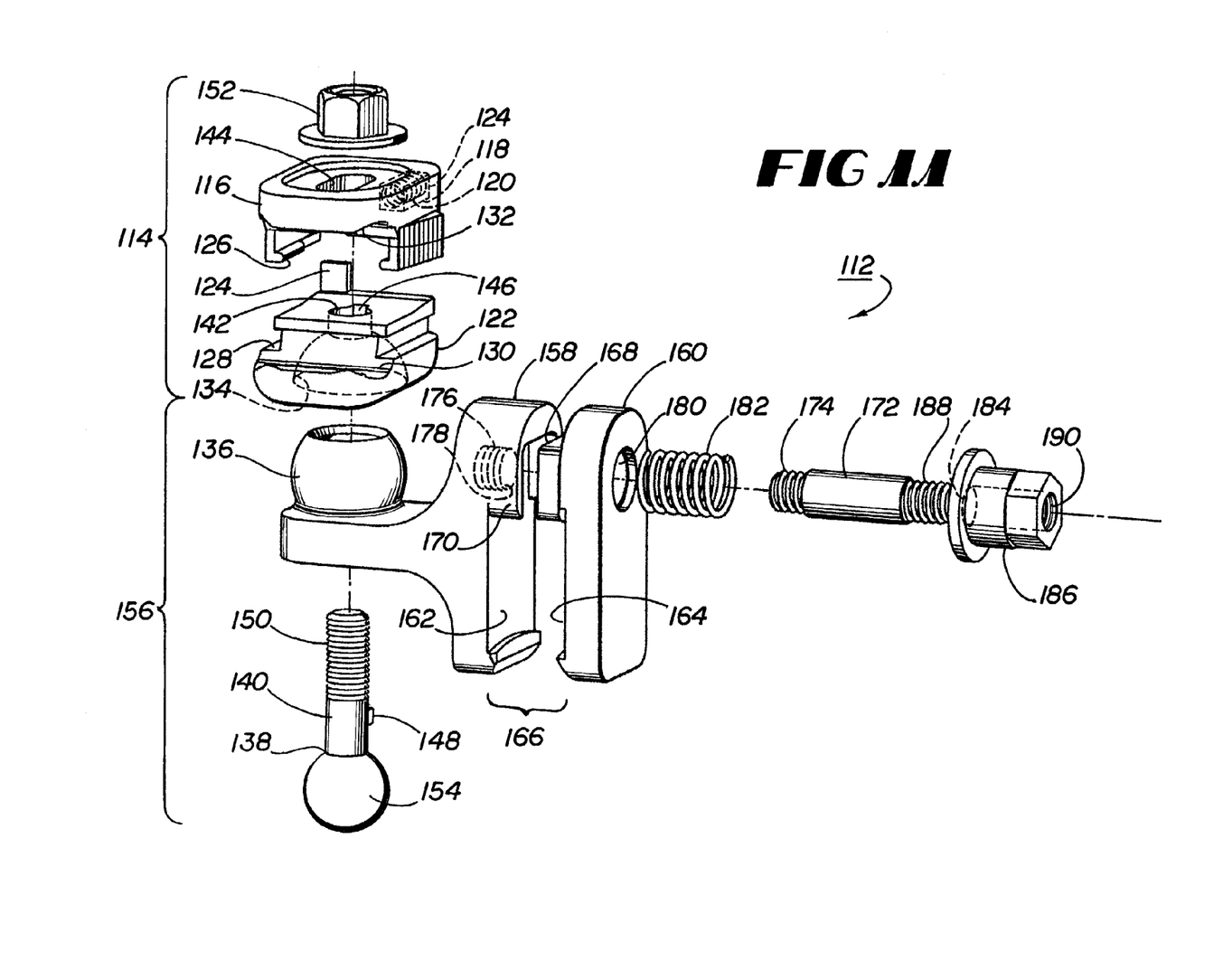
FIG. 11 is an exploded perspective view of the fixation component of FIG. 10.
Figure 12:
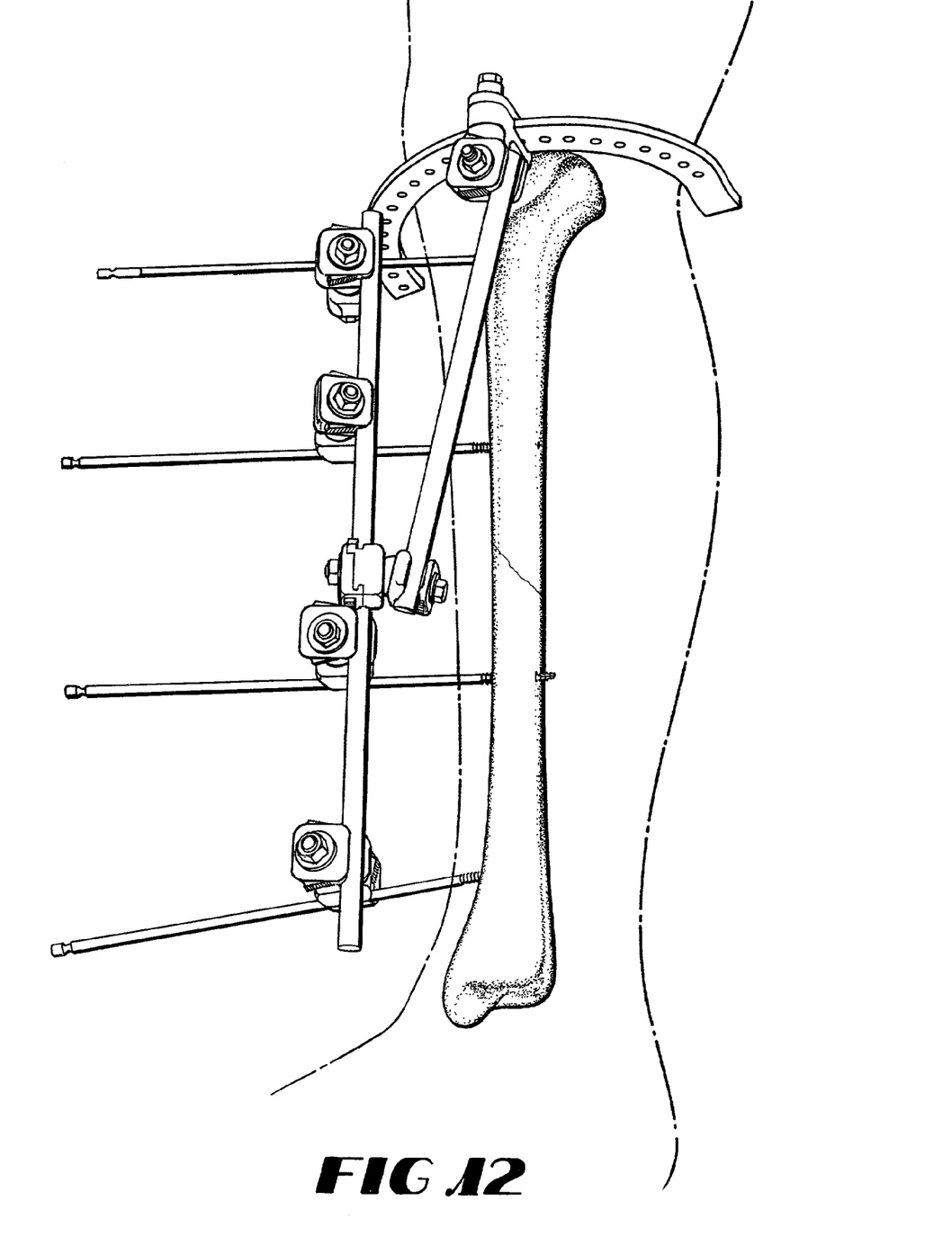
FIG. 12 is a perspective view of an external fixation system according to one embodiment of this invention.

In an alternative embodiment, a fixation component is designed for attachment to a circumferential external fixator system, such as an ILIZAROV® brand system, a SPATIAL FRAME® brand system, or other spatial frame, to achieve a hybrid external construct. In this embodiment, shown in FIGS. 10–11, the fixation component includes a capture member for retaining a bar and a capture member for retaining a half or circumferential ring having a generally rectangular cross-section. Use of a fixation component having a capture member for retaining a ring allows a surgeon to create a hybrid frame, using both a standard external fixation system and a system that includes a circumferential external frame. This hybrid system is very useful in adapting a system for treating a shaft fracture, or typical in-line fracture, to one for treating a plateau fracture, which is a fracture in a joint space. A T-component 112 according to one embodiment of a fixation component of this invention includes a second capture member 114 that is similar to the second capture member described above with respect to the bar-to-pin fixation component. Head 116 of second capture member 114 has a recess adapted to receive a spring, while base 122 of second capture member 114 includes a stop 124, and functions with recess 118 and spring 120 as described above. Second capture member 114 also includes first tracks 126 and second tracks 128 so that the head 116 and base 122 translate and retain a bar in a groove 130 and wedge 132 in the same manner as described above.

Base 122 of second capture member 114 also includes cooperating surface 134, which is adapted to receive planetary member 136 of first capture member 156. Connector 138, which, as described above and shown in FIG. 11, may be a ball stud, has shaft 140 that extends through apertures 142, 144 in the base 122 and head 116 of second capture member 114. Slot 146 in aperture 142 of base 122 is adapted to receive a key 148 on the shaft 140 of the connector 138 in order to prevent rotation of connector 138 within second capture member 114. Threads 150 on shaft 140 mate with second fastener 152, while end 154 is received in planetary member 136.

First capture member 156 includes base 158 and head 160, each having a recess 162, 164, which together form channel 166, adapted to receive a ring having a rectangular cross-section. Head 160 has extension 168 that fits into rim 170 of base 162. Rod 172 includes second threads 174 that mate with the internal threads 176 of aperture 178 of base 158 after extending through aperture 180 of head 160. Biasing element 182, such as a spring, passes over rod 172 and also into aperture 184 of first fastener 186. First threads 188 of rod 172 mate with internal threads 190 of first fastener 186. Tightening of first fastener 186 thus locks the base 158 and head 160 of first capture member 156. Second capture member 114 is free to rotate about planetary member 136 of base 158 of first capture member 156 until second fastener 152 is tightened, at which time both the second capture member 114 and the planetary member 136 and cooperating surface 134, which form the joint, are locked.

In an alternative embodiment, other locking mechanisms may be used, such as a universal joint mechanism, which allows independent movement in different directions. In yet another alternative embodiment, the capture member may include a flip through for the bar or pin, rather than a snap-on from the side as described above.

One embodiment of a fixation component of this invention is made from titanium and aluminum. In this embodiment, the heads of the capture members are made from aluminum and the remaining parts from titanium. In alternative embodiments, fixation components are made from metals, alloys, plastics, composites, ceramics, or any other suitable material.

Figure 13:
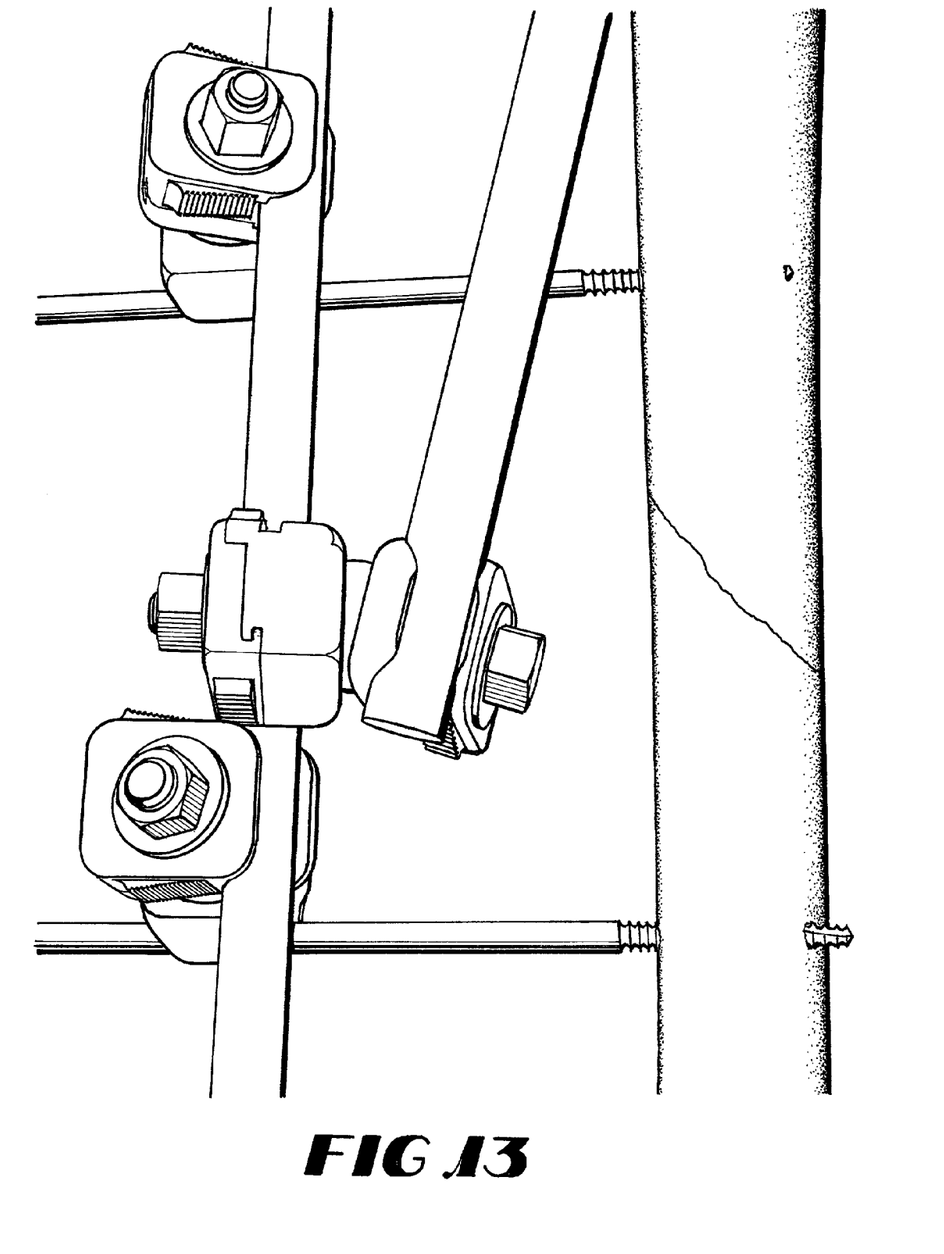
FIG. 13 is an enlarged fragmentary perspective view of selected fixation components of FIG. 12.

One method of using one form of structure according to this invention, shown in FIG. 13, which includes an improved fixation component for achieving optional external fixation of bones, is as follows:

At least two half pins are self-drilled into a bone, one on either side of a bone fracture. One bar-to-pin fixation component is connected to each pin by placing each pin into the capture member of each fixation component sized to receive a pin, such as the first capture member of the bar-to-pin fixation component shown in FIG. 1. Each fixation component is placed into the fixation component from the side for easy placement. After a pin is in place, the first fastener is tightened, so that the pin is retained in the capture member, while the second capture member and joint continue to freely rotate. Bars are then snapped into the bar capture member of the fixation components, forming a frame for the system. As each bar is added, the fixation components are adjusted as required by loosening the joint and second capture member, so that optimal positioning may be obtained. Bar-to-bar fixation components and bar-to-pin fixation components may be added to expand and connect the frame as required. If it is necessary or desirable to utilize a circumferential ring or half ring with a system for complex fractures, as shown in FIG. 13, additional fixation components having capture members designed to retain the rectangular bar of a ring are used to join the standard system to the specialized frame. A T-component is used to capture the rectangular bar of a ring and link it to a bar of the original frame, forming a hybrid system. If additional reduction is required, one capture member of any component may be loosened without losing placement of the system. A T-component may also be used to provide stability to an existing system that has already been placed using standard fixation component designs. A plurality of clamps may be used in various configurations to achieve stability for different fractures.

Similar instrumentation and devices may be used in other areas, such as to provide a fixed reference to a pin. Constructs made under the present invention are stable and provide for a wide variety or placements. Embodiments of an external fixation component according to this invention may also be adapted for use with an image guided surgery system to provide stability to a reference frame or other guidance target or mechanism.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. An external fixation component comprising:
  (a) a first capture member adapted to capture a first element of an orthopedic fixation system;
  (b) a second capture member adapted to capture a second element of an orthopedic fixation system and coupled to the first capture member such that the coupling allows the first capture member and the second capture member to rotate about three axes relative to each other;

wherein (i) the coupling is adapted to secure the first and second capture members from rotation with a single activation, (ii) the second capture member is adapted to capture the second element by snapping onto the second element from a direction generally perpendicular to the longitudinal axis of the second element, and (iii) each of the first and second capture members further comprises a base and a head;

(c) a connector;

(d) internal threads in an aperture of the base of the first capture member, wherein the aperture is adapted to receive a first fastener;

(e) a first fastener comprising a threaded end adapted to mate with the internal threads of the base;

(f) a biasing member adjacent an end of the connector and wherein the threaded end of the first fastener is adjacent the biasing member; and (g) threads on a second portion of the connector adapted to mate with threads on a second fastener.

2. The component of claim 1 wherein one capture member may be locked while the other capture member is capable of rotation.

3. The component of claim 1 wherein tightening the first fastener locks the first capture member and tightening the second fastener locks the second capture member.

4. The component of claim 1 wherein the head of each capture member further comprises a grip surface.

5. The component of claim 1 wherein the head of each of the capture members further comprises a wedge and the base of each of the capture members further comprises a groove.

6. The component of claim 5 wherein the wedge and groove of each capture member form a channel adapted to receive a fixation element.

7. The component of claim 5 wherein the grooves further comprise splines.

8. The component of claim 1 wherein for each capture member, the head and the base are slidably coupled.

9. The component of claim 8 wherein the base and head each further comprise at least one track along which the head and base translate with respect to each other.

10. The component of claim 8 wherein the base further comprises a stop and the head further comprises a recess adapted to receive a biasing member.

11. The component of claim 1 wherein one capture member is adapted to receive a bar and the other capture member is adapted to receive a pin.

12. The component of claim 1 wherein each capture member is adapted to receive a bar.

13. The component of claim 1 wherein one capture member is adapted to receive a bar and the other capture member is adapted to receive a wire.

14. The component of claim 1 wherein the first capture member is adapted to capture the first element by snapping onto the first element from a direction generally perpendicular to the longitudinal axis of the first element.

15. The component of claim 1 wherein one capture member is adapted to receive at least a partial ring and the other capture member is adapted to receive a bar.

16. An external fixation component comprising:

(a) a first capture member comprising:
  (i) a planetary member having inner and outer surfaces and including an aperture adapted to receive a connector,
  (ii) a partially enclosed channel adapted to capture a fixation element; and (b) a second capture member comprising:
  (i) a cooperating surface adapted to receive and correspond generally in shape with the outer surface of the planetary member and an aperture adapted to receive a connector,
  (ii) a partially enclosed channel adapted to capture a fixation element; and (c) a connector comprising:
  (i) a first portion that corresponds generally in shape to and is adapted to be received in the inner surface of the planetary member, and
  (ii) a second portion adapted to extend through the aperture in the cooperating surface of the second capture member;

wherein when the first portion of the connector is urged against the inner surface of the planetary member and locked, and the outer surface of the planetary member is urged against the cooperating surface and locked, the fixation elements are oriented and locked in position relative to each other, and wherein when unlocked, each capture member is able to rotate about more than one axis relative to the other capture member.

17. The component of claim 16 wherein the first portion of the connector comprises an end and the second portion of the connector comprises a shaft.

18. The component of claim 16 wherein the connector further comprises a key adapted to be received in a slot in the second capture member.

19. The component of claim 16 wherein the first portion of the connector is generally spherical.

20. The component of claim 16 further comprising a biasing member adjacent the first portion of the connector.

21. The component of claim 16 wherein the planetary member is generally spherical.

22. The component of claim 16 wherein the cooperating surface is generally spherical.

23. The component of claim 16 wherein the inner surface of the planetary member is tapered.

24. The component of claim 16 wherein the cooperating surface is tapered.

25. The component of claim 16 wherein the planetary member is textured.

26. The component of claim 16 wherein the cooperating surface is textured.

27. The component of claim 16 wherein the cooperating surface comprises tungsten cobalt carbide and has a coating.

28. The component of claim 16 wherein the planetary member further comprises a mechanical locking pattern.

29. The component of claim 28 wherein the mechanical locking pattern comprises splines.

30. The component of claim 16 herein the cooperating surface further comprises a mechanical locking pattern.

31. The component of claim 30 wherein the mechanical locking pattern comprises splines.

32. The component of claim 16 wherein the first capture member is capable of rotating in three axes relative to the second capture member.

33. The component of claim 16 wherein the second capture member is capable of rotating in three axes relative to the first capture member.

34. The component of claim 16 wherein one capture member may be locked while the other capture member is capable of rotation.

35. The component of claim 16 wherein each of the first and second capture members further comprise a base and a head.

36. The component of claim 35 further comprising:
(a) internal threads in an aperture of the base of the first capture member, wherein the aperture is adapted to receive a first fastener;
(b) a first fastener comprising a threaded end adapted to mate with the internal threads of the base;
(c) a biasing member adjacent the end of the connector and wherein the threaded end of the first fastener is adjacent the biasing member; and
(d) threads on the second portion of the connector adapted to mate with threads on a second fastener.

37. The component of claim 16 wherein tightening the first fastener locks the first capture member and tightening the second fastener locks the second capture member.

38. The component of claim 35 wherein the head of each capture member further comprises a grip surface.

39. The component of claim 35 wherein the head of each of the capture members further comprises a wedge and the base of each of the capture members further comprises a groove.

40. The component of claim 39 wherein the wedge and groove of each capture member form each partially enclosed channel.

41. The component of claim 39 wherein the grooves further comprise splines.

42. The component of claim 16 wherein each of the first and second capture members comprise:
(a) a base; and
(b) a head slidably coupled to the base;
wherein the base slides transverse to the longitudinal axis of the fixation element, and the head is biased toward the fixation element.

43. The component of claim 42 wherein the base and head each further comprise at least one track and wherein the head and base translate with respect to each other along the at least one track of the base and the at least one track of the head.

44. The component of claim 43 wherein the base further comprises a stop and the head further comprises a recess adapted to receive a biasing member.

45. The component of claim 16 wherein one capture member is adapted to receive a bar and the other capture member is adapted to receive a pin.

46. The component of claim 16 wherein each capture member is adapted to receive a bar.

47. The component of claim 16 wherein one capture member is adapted to receive a bar and the other capture member is adapted to receive a wire.

48. The component of claim 16 wherein the first and second capture members each comprise a slot extending toward an end of the capture members.

49. The component of claim 16 wherein one capture member is adapted to receive at least a partial ring and the other capture member is adapted to receive a bar.

50. An external fixation system comprising:
a plurality of fixation elements;
a plurality of fixation components, at least one of the plurality of fixation components comprising:
(a) a first capture member adapted to capture a first element of an orthopedic fixation system; and
(b) a second capture member adapted to capture a second element of an orthopedic fixation system and coupled to the first capture member such that the coupling allows the first capture member and the second capture member to rotate about three axes relative to each other;
wherein (i) the coupling is adapted to secure the first and second capture members from rotation with a single activation, (ii) the second capture member is adapted to capture the second element by snapping onto the second element from a direction generally perpendicular to the longitudinal axis of the second element, and (iii) each of the first and second capture members further comprises a base and a head;
(c) a connector;
(d) internal threads in an aperture of the base of the first capture member, wherein the aperture is adapted to receive a first fastener;
(e) a first fastener comprising a threaded end adapted to mate with the internal threads of the base;
(f) a biasing member adjacent an end of the connector and wherein the threaded end of the first fastener is adjacent the biasing member; and
(g) threads on a second portion of the connector adapted to mate with threads on a second fastener.

51. The fixation system of claim 50 wherein the fixation elements comprise at least one bar.

52. The fixation system of claim 50 wherein the fixation elements comprise at least one pin.

53. The fixation system of claim 50 wherein the fixation elements comprise at least one wire.

54. The fixation system of claim 50 wherein one capture member may be locked while the other capture member is capable of rotation.

55. The fixation system of claim 50 wherein tightening the first fastener locks the first capture member and tightening the second fastener locks the second capture member.

56. The fixation system of claim 50 wherein the head of each capture member further comprises a grip surface.

57. The fixation system of claim 50 wherein the head of each of the capture members further comprises a wedge and the base of each of the capture members further comprises a groove.

58. The fixation system of claim 57 wherein the wedge and groove of each capture member form a channel adapted to receive a fixation element.

59. The fixation system of claim 57 wherein the grooves further comprise splines.

60. The fixation system of claim 50 wherein the head and the base of each capture member are slidably coupled.

61. The fixation system of claim 60 wherein the base and head each further comprise at least one track along which the head and base translate with respect to each other.

62. The fixation system of claim 60 wherein the base further comprises a stop and the head further comprises a recess adapted to receive a biasing member.

63. The fixation system of claim 50 wherein one capture member is adapted to receive a bar and the other capture member is adapted to receive a pin.

64. The fixation system of claim 50 wherein each capture member is adapted to receive a bar.

65. The fixation system of claim 50 wherein one capture member is adapted to receive a bar and the other capture member is adapted to receive a wire.

66. The fixation system of claim 50 wherein the fixation elements comprise at least one ring.

67. The fixation system of claim 50 wherein one capture member is adapted to receive at least a partial ring and the other capture member is adapted to receive a bar.

* * * * *